United States Patent [19]
Weldon et al.

[11] Patent Number: 5,129,882
[45] Date of Patent: Jul. 14, 1992

[54] WOUND CLOTTING DEVICE AND METHOD OF USING SAME

[75] Inventors: Thomas D. Weldon; Charles Larsen, both of Aguadilla

[73] Assignee: Novoste Corporation, Aquadilla, P.R.

[21] Appl. No.: 634,406

[22] Filed: Dec. 27, 1990

[51] Int. Cl.⁵ .............................................. A61M 29/00
[52] U.S. Cl. ................................. 604/96; 606/213; 604/53; 604/171
[58] Field of Search ................... 604/27, 38, 46–47, 604/52, 57, 59–60, 93, 96, 171, 173, 218, 235, 310, 311, 11, 285, 286, 287, 890.1; 606/213

[56] References Cited

U.S. PATENT DOCUMENTS

| | | |
|---|---|---|
| 682,090 | 9/1901 | Lee . |
| 3,833,003 | 9/1974 | Taricco ................... 604/53 |
| 4,654,025 | 3/1987 | Cassou et al. ........... 604/55 |
| 4,744,364 | 5/1988 | Kensey ................. 128/334 R |
| 4,852,568 | 8/1989 | Kensey ................. 128/325 |
| 4,890,612 | 1/1990 | Kensey ................. 606/213 |
| 4,900,303 | 2/1990 | Lemelson ............... 604/54 |
| 5,021,059 | 6/1991 | Kensey et al. ......... 606/213 |

Primary Examiner—C. Fred Rosenbaum
Assistant Examiner—C. Maglione
Attorney, Agent, or Firm—Cook, Egan, McFarron and Manzo, Ltd.

[57] ABSTRACT

A wound clotting device is disclosed comprising a clotting device for dispensing a clotting agent onto a selected location in a patient while being retained adjacent to that location, comprising a tube having a proximal end portion and a distal end portion; means defining an inflation lumen in said tube extending between said proximal and distal end portions; inflatable retention means carried by said tube at said distal end portion for retaining said distal end at a selected location within the body of a living patient, said retention means being in fluid communication with said inflation lumen; means defining a second lumen in said tube extending between said proximal and distal end portions; means for receiving a quantity of clotting agent located within said second lumen; and means disposed within said second lumen for dispensing said clotting agent from said distal end of said second lumen to deposit said clotting agent at said selected location within a patient. A method for using such clotting device is also disclosed.

7 Claims, 3 Drawing Sheets

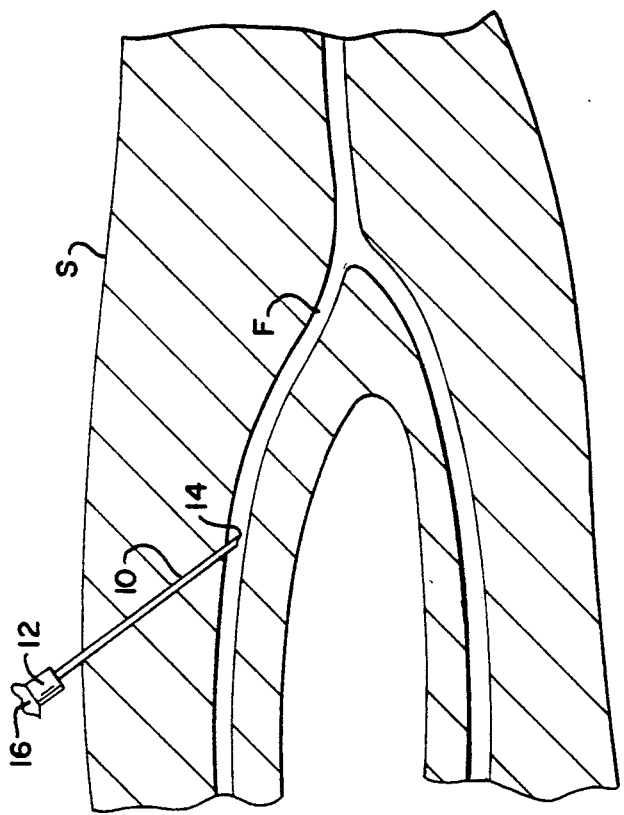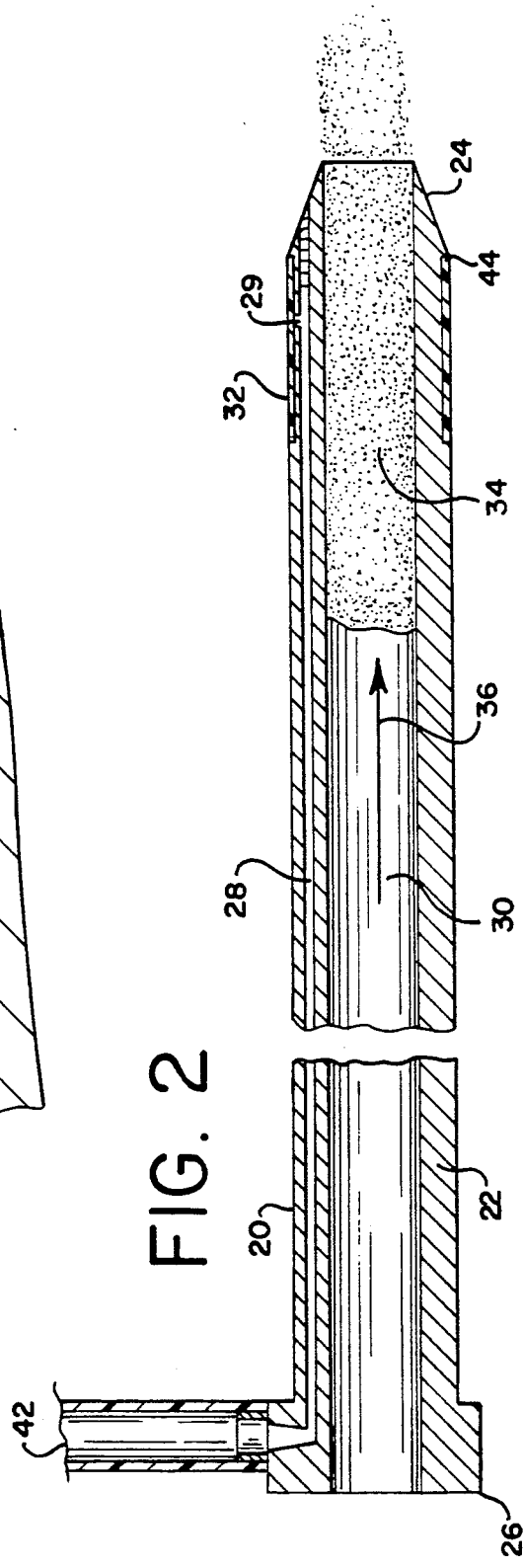

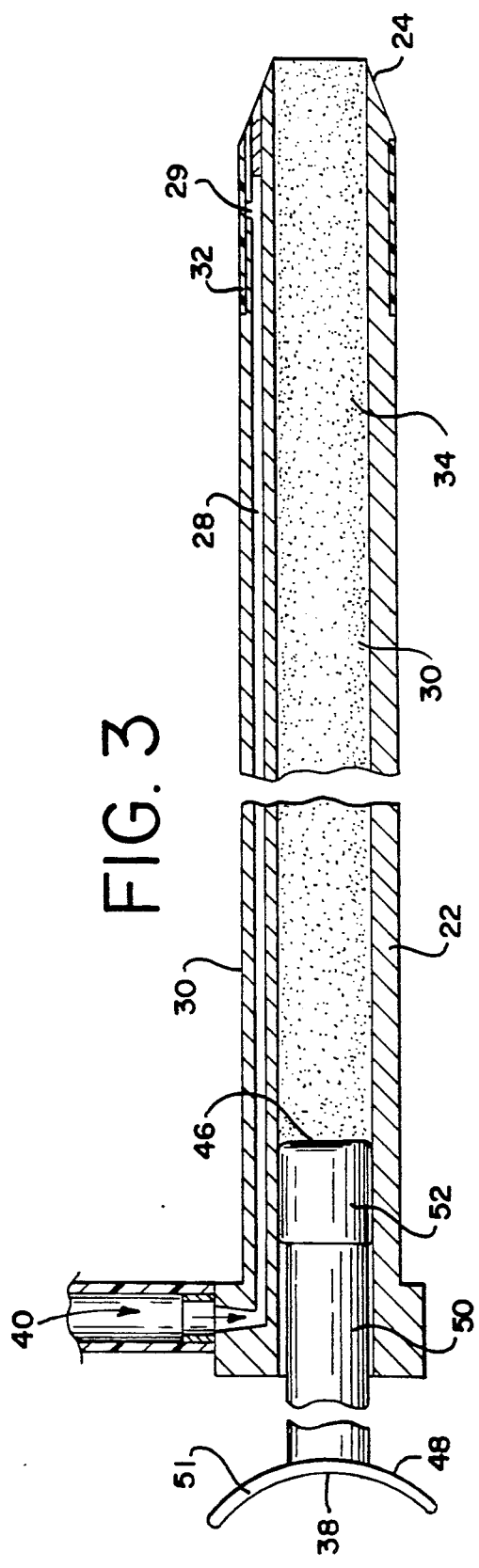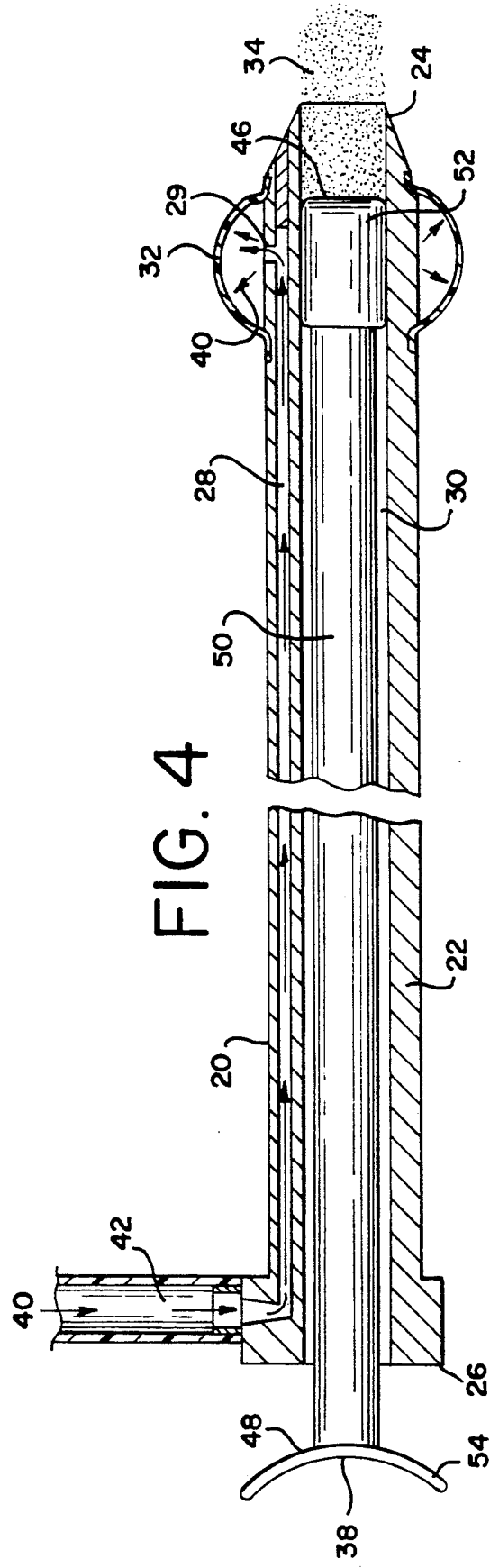

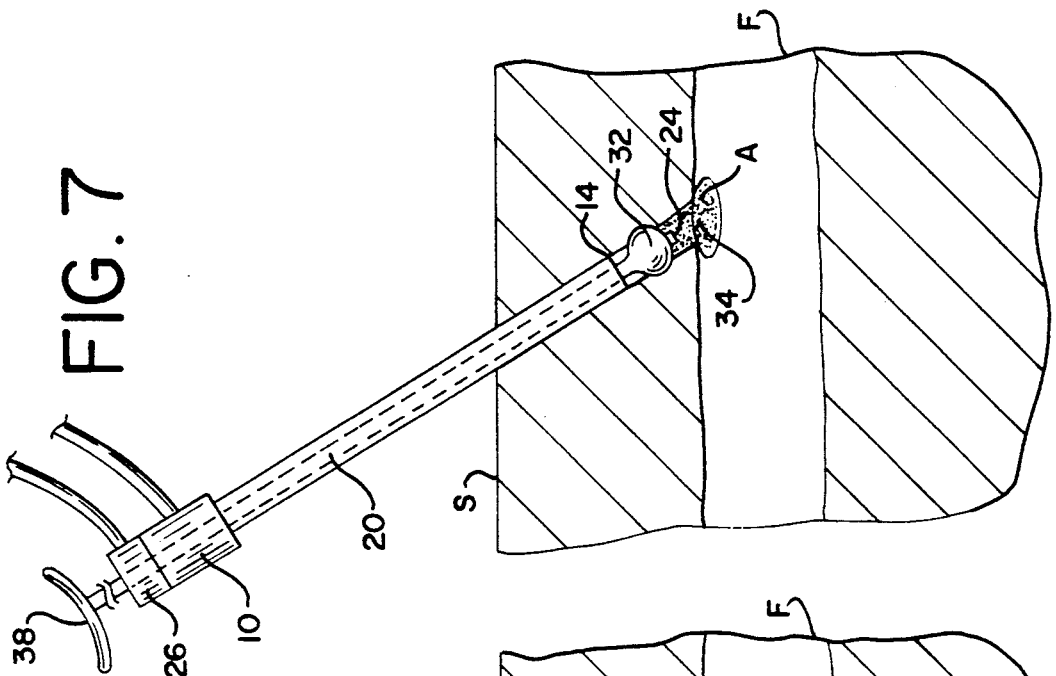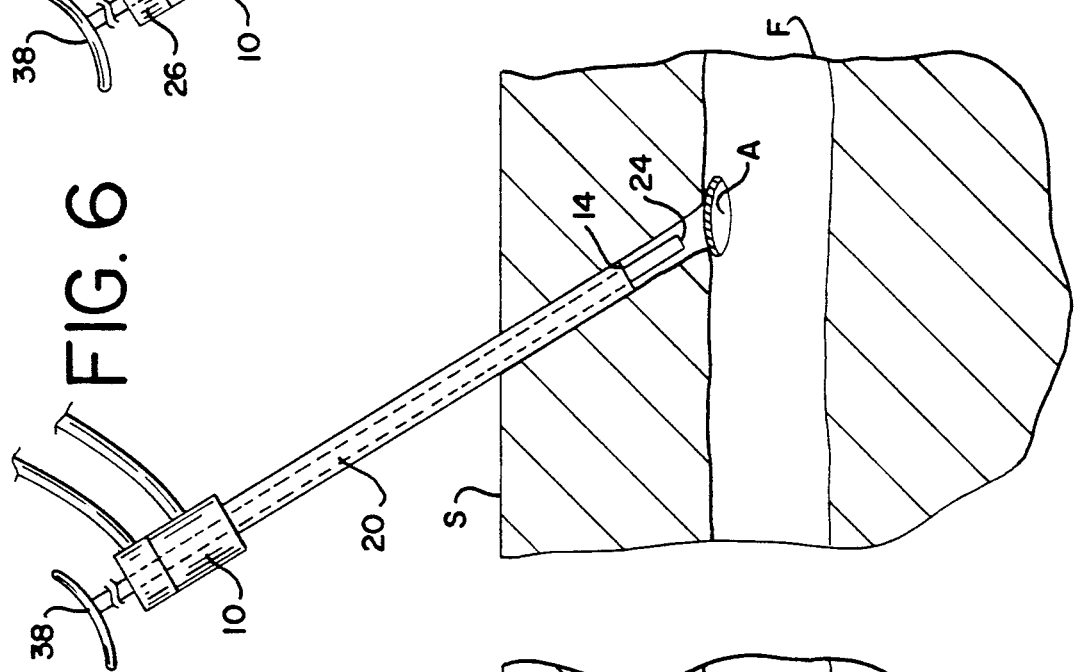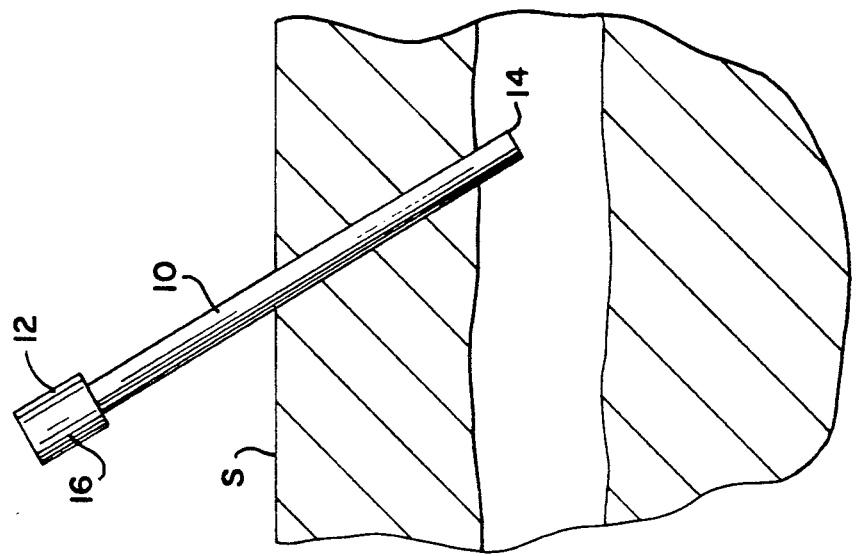

WOUND CLOTTING DEVICE AND METHOD OF USING SAME

DESCRIPTION

Background

The present invention relates, in general, to devices and methods for stopping an undesirable flow of fluid between two contiguous tissue samples, such as bleeding from a blood vessel after removal of a medical device, catheter system, or the like. More particularly, the present invention concerns a novel clotting device which includes means for depositing a clotting agent at a wound or aperture between two contiguous tissue areas, such as the opening in a blood vessel or the like following removal of a medical device or instrument therefrom. The present invention also concerns a novel method for using such a clotting device.

Many medical procedures, including both therapeutic and diagnostic procedures, require access between two contiguous tissue samples, such as through the skin and into the vascular system of the patient. For example, although various means may be used to obtain access into a vein or artery, typically access is obtained by inserting a cannula or catheter (called an introducer catheter or sheath) through the skin and into the selected blood vessel. A medical or diagnostic instrument, such as a guide wire, guiding catheter, balloon angioplasty device, atherectomy device, or the like is then inserted into the vascular system through the introducer catheter.

Depending on the procedure, to permit the insertion of the diagnostic or therapeutic device therethrough, the introducer sheath must be of relatively large diameter. This, of course, results in a relatively large hole or aperture in the vessel wall. After the medical procedure is completed, however, this aperture must be closed, and bleeding from the blood vessel stopped.

A common technique to stop such bleeding, as in cardiac balloon angioplasty procedures, is for a nurse or technician to apply continuous pressure on the aperture in the blood vessel until the blood within the aperture clots. This may require an hour or more of medical personnel time. Unfortunately, when this procedure is utilized, there is a significant chance that upon movement by the patient, the aperture will reopen and begin bleeding again, resulting in a hematoma or other complications. Because of the risk of a hematoma, patients are usually required to remain overnight in the hospital for rest and observation, thus greatly increasing the cost of the overall procedure.

One prior device for stopping bleeding from an aperture in a blood vessel is a type of expandable plug. The plug is pushed through the opening into the blood vessel and into the blood stream. Once in the blood stream, it expands. The expanded plug is then pulled back against the aperture where, because of its expanded size, it plugs the opening. Such a device may work satisfactorily, but requires inserting and leaving a foreign object in the vessel. It is usually medically preferable to avoid inserting and leaving objects in a vessel.

Accordingly, it is a general object of the present invention to provide a clotting device, as well as a method for using such device, which are particularly useful in clotting vascular wounds resulting from insertion of a medical device, and which do not suffer from the drawbacks described above.

SUMMARY OF THE INVENTION

The wound clotting device of the present invention comprises, in general, a tube having proximal and distal end portions and an inflation lumen extending between the proximal and distal ends. An inflatable retention means, which is in fluid communication with the inflation lumen, is carried at the distal end of the device for retaining the device at a selected location within the body of the patient. A second or dispensing lumen also extends between the proximal and distal ends of the device, and has means for receiving a quantity of clotting agent therewithin. Dispensing means are also located within the second lumen for dispensing the clotting agent from the distal end of the second lumen at the selected location within the patient.

To allow the clotting device to be packaged as a preassembled unit, the clotting agent is preferably predisposed in the second lumen. However, the clotting agent may also be inserted into the lumen at a later time, such as at the time of the procedure, without departing from the present invention.

For dispensing the clotting agent, a plunger or piston may be located within the second lumen. By advancing the plunger or piston, the clotting agent may be dispensed in a selected amount and rate, as prescribed by the physician, for the particular wound.

The clotting device of the present invention is preferably inserted into the patient through the introducer cannula or a sheath utilized in the preceding medical procedure. Accordingly, the tube should have a sufficiently small diameter so as to fit into the introducer. Further, the tube should be of a sufficient length so that the distal end of the tube may be advanced sufficiently beyond the distal end of the introducer to allow positioning of the distal end of the tube adjacent to the aperture and inflation of the retention means.

The inflatable retention means of the present invention preferably comprises a sleeve of flexible material disposed on the distal end portion of the tube. Each end of the sleeve is preferably adhered or bonded to the surface of the tube to define an inflatable balloon portion therebetween which is in communication with the inflation lumen and which, when inflated, will hold the distal end of the clotting device adjacent to an opening or aperture in the blood vessel in the patient. The sleeve may be disposed within a reduced diameter or recessed area at the distal end of the tube so that the clotting device has a continuous smooth exterior surface.

Further according to the present invention, clotting of an aperture in a blood vessel may be performed utilizing a wound clotting device as described above. Following removal of the diagnostic or therapeutic device, the introducer cannula is retracted from the blood vessel until the distal end of the introducer is in the proximity of, but spaced from the exterior of the blood vessel. While the introducer is at that position, the distal end of the wound clotting device of the present invention is inserted into the introducer and advanced until it extends beyond the distal end of the introducer and is adjacent to the opening or aperture in the blood vessel. The inflatable retention means on the distal end of the device is then inflated to hold the distal end adjacent to the blood vessel. The clotting agent is dispensed from the distal end of the device and onto the blood vessel at the site of the aperture. The clotting agent will assist in stopping bleeding from the blood vessel by causing the blood in the aperture to clot more rapidly than normal, thus reducing the amount of bleeding and reducing the risk of post-surgery hematoma. The inflated retention means may also serve to reduce bleeding during the clotting time. The retention means is then deflated, and the clotting device and the introducer sheath are withdrawn from the patient, leaving no substantial foreign matter within the vessel of the patient as a result of this method.

These and other features and advantages of the present invention will become more apparent from the following detailed description of the invention, as exemplified in the accompanying drawings.

BRIEF DESCRIPTION OF THE DRAWINGS

FIG. 1 is a fragmentary diagrammatic view of a sheath introducer extending through the skin into a femoral artery of a patient.

FIG. 2 is an enlarged cross-sectional view of the proximal and distal end portions of a wound clotting device of the present invention with a means for dispensing a clotting agent shown diagrammatically.

FIG. 3 is a cross-sectional view showing the proximal and distal ends of one embodiment of the wound clotting device of the present invention utilizing a plunger for dispensing the clotting agent and containing a quantity of clotting agent.

FIG. 4 is a cross-sectional view of the clotting device of FIG. 3 showing the inflatable retention means inflated and a plunger ejecting the clotting agent from the device's distal end.

FIG. 5 is a side view of a sheath introducer which has been introduced through the skin and into a blood vessel.

FIG. 6 is a side view depicting one of the steps of the method of the present invention, utilizing the wound clotting device depicted in FIGS. 2, 3, and 4, where the sheath introducer of FIG. 5 has been retracted from the blood vessel and the wound clotting device has been inserted into the introducer.

FIG. 7 is a side view depicting another of the steps of the method of the present invention where the clotting device of FIGS. 2, 3, and 4 is utilized to dispense clotting agent onto an aperture in a blood vessel.

DETAILED DESCRIPTION OF THE INVENTION

FIG. 1 is a partial diagrammatic representation of a sheath introducer 10 which has been advanced through the skin surface S into a femoral artery F of a living patient. The sheath introducer 10 is shown in the femoral artery F for purposes of illustration only and not for purposes of limitation. It is understood that a sheath introducer can be used in accessing other arteries, veins, or blood vessels, or in communicating between other contiguous tissue areas of a patient's body.

As shown in the exemplary procedure of FIG. 1, the sheath introducer 10 is initially advanced through a patient's skin and into the artery F. The sheath introducer 10 has a resealable valve 12 located at its proximal end 16, as is well known in the medical field. In the typical procedure, some type of medical device, for example, a guiding catheter, an angioplasty device, or the like, is inserted into the sheath introducer through the valve and advanced into the artery and then to the location of the procedure. After the medical device has been used, it is withdrawn from the artery and the sheath introducer. The sheath introducer 10 must then be removed from the artery F. This, of course, leaves an aperture or opening in the artery F (See FIGS. 6 and 7). To assist in stopping bleeding from the aperture in the artery, the wound clotting device of the present invention may be utilized.

FIGS. 2, 3, and 4 show, in an enlarged view, various embodiments of the wound clotting device of the present invention. With reference to these figures, the wound clotting device 20 of the present invention comprises a tube, generally at 22, with a distal end portion generally at 24 and a proximal end portion generally at 26. A relatively large second lumen 30 and a smaller inflation lumen 28 extend between the proximal end 26 to the distal end 24 of the tube 22. The second lumen 30 is open at the distal end, and the distal end of the inflation lumen is sealed closed.

The tube may be formed by extrusion from a suitable plastic such as nylon, polypropylene, or the like, although the present invention is not limited by the method of manufacture or the type of material, and injection molding or other materials could be used where feasible. The plastic material utilized in the manufacture of the tube should in any event, be sufficiently stiff so as to be capable of being advanced through an introducer cannula or sheath introducer, but not so stiff that it will cause damage to tissue.

The inflation lumen 28 extends fully between the proximal end and distal ends of the tube 22. As noted above, the inflation lumen is sealed at the distal end and carries a valve (not shown) at the other end, through which an inflation fluid, such as sterile water, may be injected. Such valves are well known in medical product design and thus it will not be described in detail here. The diameter of the inflation lumen may vary, depending on the particular application. Typically, however, the diameter should be sufficiently large to permit ready inflation of the retention means.

In the preferred embodiment of the wound clotting device, an inflatable retention means 32 is located on the distal end 24 of the tube 22, although other types or forms of retention means may also be used for retaining the distal end of the clotting device at a selected position. The preferred inflatable retention means 32 comprises a flexible sleeve located within a recessed area 44 at the distal end 24 of the tube 22. Each end of the sleeve is adhered or bonded to the surface of the tube, within the recessed area, to define an inflatable balloon portion therebetween. Any suitable solvent, adhesive, or the like may be used to adhere or bond the sleeve to the tube. Inflation aperture 29 extends through the wall of the tube, to provide a fluid flow path between the inflation lumen and the unadhered portion of the sleeve, to permit inflation of the balloon. The sleeve and recessed area preferably have the same length and the recessed area is preferably recessed an amount equal to the thickness of the sleeve, so that the exterior surface of the tube will be smooth and essentially uninterrupted after the sleeve is attached.

To assist in forming a blood clot at the site of the vessel aperture, a quantity of clotting agent 34 is preferably located in the second lumen 30, for ejection onto the aperture or wound. The clotting agent may be any of the suitable clotting agents presently commercially available. For example, the clotting agent 34 may be a thrombin agent. A thrombin agent is frequently used as a topical treatment by vascular surgeons to stop surface bleeding after a large incision is made in the body. By dispensing thrombin agent onto an aperture in an artery, bleeding from the aperture can be reliably stopped, reducing the risk of a hematoma, and eliminating the need for an overnight stay in the hospital. The clotting agent, which is preferably in foam, powder, or jell form, may be pre-filled into the second lumen during manufacture or may be inserted into the second lumen at the time of the procedure.

The clotting agent is deposited at the site of the aperture or wound from the distal end of the tube 22. The means, generally at 36, for dispensing the clotting agent 34 is preferably a plunger 38, as shown in FIGS. 3 and 4. The plunger 38 has a distal end, generally at 46, and a proximal end, generally at 48. A rod 50 extends between the distal and proximal ends of the plunger. A piston or grommet 52 is located at the distal end of the rod 50 and a thumb rest 54 is provided on the proximal end. By advancing the plunger 38, the piston 52 forces the clotting agent 34 from the distal end 24 of the tube 22. Calibrations may be provided on the rod and/or tube to provide an indication of the amount of clotting agent dispensed and the rate of dispensing. In FIG. 3, the piston 52 of the plunger 38 is nearer the proximal end 26 of the tube 22 and has not yet been advanced towards the distal end 24 of the tube 22. FIG. 4 illustrates the piston 52 being advanced towards the distal end 24 of the tube 22, ejecting the clotting agent 34. FIG. 4 also depicts inflation of the retention means 32 by injection of a fluid 40 into the inflation lumen 28 to retain the distal end 24 at some selected location in the patient.

Use of the present invention in forming a vascular clot is depicted diagrammically in FIGS. 5-7. FIG. 5 shows an introducer cannula, for example the sheath introducer 10, which previously has been inserted through the skin surface into a femoral artery F, and following removal of the particular medical device.

As shown in FIG. 6, the introducer 10 is retracted out of the artery F, leaving an aperture or opening A in the wall of the artery F. The introducer 10 is retracted until it is out of the artery and spaced from the artery (although it is not completely removed, and remains in the proximity of the artery). The wound clotting device 20, as described above, is then inserted through the valve 12 of the introducer 10 and into the introducer 10. The clotting device 20 is then advanced through the introducer 10 until the distal end 24 of the clotting device 20 extends beyond the distal end 14 of the introducer 10 and is adjacent to the aperture A in the artery F. To assure that the clotting device is advanced the proper amount, the clotting device may be of a selected length for each particular brand of introducer sheath used, or have indicia along the length of the tube 22 to indicate how far it should be advanced for each particular brand of introducer sheath.

As shown in FIG. 7, the inflatable retention means 32 is then inflated to hold the distal end 24 of the clotting device 20 adjacent to the artery F. Accordingly, the distal end 24 cannot be pushed into the aperture A or pulled away from the aperture A. The plunger 38 is then advanced and the clotting agent 3 is dispensed from the distal end 24 of the clotting device 20 and onto the aperture A of the artery F. The clotting agent 34 will greatly hasten clotting and prevent further bleeding from the aperture A.

In another embodiment of the method, the inflatable retention means 32, on the distal end 24 of the clotting device 20, is pressed and held against the aperture A in the artery F. This step is done after the retention means 32 has been inflated and the clotting agent has been dispensed onto the aperture A. By pressing the inflatable retention means 32 against the artery F, pressure is put on the aperture A to assist the clotting agent 34 in clotting the bleeding from the aperture A.

Finally, the clotting device 20 and the introducer 10 are withdrawn from the patient's body, leaving no substantial amount of foreign material within the patient's vascular system.

The features of the wound clotting device of the present invention and the method for using the clotting device have been described in connection with the accompanying drawings for purposes of illustration and not limitation. It is intended that this application include those modifications, variations and additions that would be readily apparent to one of ordinary skill upon reading this description. Accordingly, for ascertaining the scope of the present invention, reference must be made to the appended claims.

We claim:

1. A wound clotting device comprising the combination of a sheath introducer, a tube, a clotting agent and means for ejecting said clotting agent;

said sheath introducer having proximal and distal end portions and being of sufficient length to extend through the skin of a living patient into the vicinity of a blood vessel located within the patient;

said tube being elongated with proximal and distal end portions and adapted for advancement into said sheath introducer and being of sufficient length to extend beyond the distal end of said introducer, said tube comprising an inflation lumen and a second lumen extending between said proximal and distal ends;

inflatable retention means carried at said distal end of said tube, in fluid communication with said inflation lumen, and disposed to inflate and to hold said distal end adjacent to said blood vessel in said patient when the distal end of said tube is advanced beyond the distal end of said introducer;

said clotting agent being located within the second lumen of said tube; and said means for ejecting said clotting agent being located within said second lumen of said tube so as to dispense said clotting agent from said distal end of said second lumen to a selected location along said blood vessel within said patient.

2. The wound clotting device according to claim 1 wherein said means for ejecting said clotting agent is a plunger.

3. The wound clotting device according to claim 1 wherein said inflatable retention means comprises a flexible sleeve disposed on said distal portion of said tube, said sleeve being adhered to said tube at each end of said sleeve to define an inflatable balloon portion of said sleeve which, when inflated, will hold said clotting device adjacent to an opening in said blood vessel within said patient.

4. The wound clotting device according to claim 1 wherein said tube has means at its proximal end portion for receiving fluid into said inflation lumen to inflate said retention means to hold said wound clotting device adjacent to an opening in said blood vessel within said patient.

5. A method for treating vascular wounds through which an introducer cannula had been advanced comprising:

retracting the introducer cannula from a blood vessel until the distal end of said cannula is adjacent to the exterior of the blood vessel;

inserting a clot forming device into said introducer cannula, said device comprising:

a tube having a proximal end portion and a distal end portion;

means defining an inflation lumen in said tube extending between said proximal and distal end portions;

inflatable retention means carried by said tube at said distal end portion for retaining said distal end at a selected location within the body of a living patient, said retention means being in fluid communication with said inflation lumen;

means defining a second lumen in said tube extending between said proximal and distal end portions, a quantity of clotting agent located within said second lumen, within said second lumen for dispensing said clotting agent from said distal end of said second lumen to deposit said clotting agent at said selected location within a patient;

advancing the clot forming device through the introducer until the distal end thereof extends beyond the distal end of the introducer cannula and is adjacent to the aperture in said blood vessel;

inflating said inflatable retention means to hold said distal end adjacent to said blood vessel;

dispensing said clotting agent from said distal end of said clotting device onto said blood vessel;

deflating said retention means; and withdrawing the clotting device and introducer cannula from the patient.

6. A method for treating vascular wounds according to claim 5 wherein said clotting agent is dispensed onto said blood vessel by ejecting said clotting agent from said distal end of said clotting device by pushing on a plunger in said second lumen of said device causing ejection of said clotting agent from the distal end.

7. A method for treating vascular wounds according to claim 5 including the step of pushing and holding said inflatable retention means against said blood vessel after said clotting agent has been dispensed.

* * * * *